Figure 1:
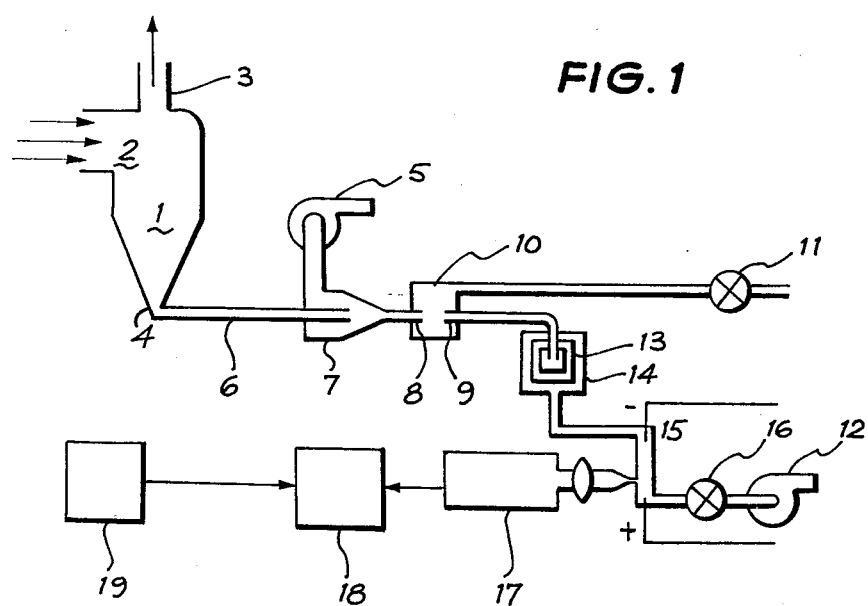

United States Patent [19]

Macourt

[11] 4,221,482
[45] * Sep. 9, 1980

[54] MINERAL PROSPECTING BY THE DETECTION OF RADON OR IODINE

[76] Inventor: Denis J. C. Macourt, 73, Dickson Ave., Artarmon, 2064, New South Wales, Australia

[ * ] Notice: The portion of the term of this patent subsequent to Jan. 30, 1996, has been disclaimed.

[21] Appl. No.: 817,498

[22] Filed: Jul. 20, 1977

Related U.S. Application Data

[63] Continuation-in-part of Ser. No. 739,110, Nov. 5, 1976, Pat. No. 4,136,951.

[30] Foreign Application Priority Data

Jul. 20, 1976 [AU] Australia .............................. PC6695
Jun. 3, 1977 [AU] Australia .............................. PD0337

[51] Int. Cl.² .......................... G01N 1/00; G01J 3/00
[52] U.S. Cl. ................................ 356/36; 23/230 EP; 356/316
[58] Field of Search .......................... 356/36, 85, 316; 23/230 EP; 250/255

[56] References Cited

U.S. PATENT DOCUMENTS

| | | | |
|---|---|---|---|
| 2,330,829 | 10/1943 | Lundberg et al. | 250/255 |
| 3,759,617 | 9/1973 | Barringer | 356/36 |
| 3,868,222 | 2/1975 | Barringer | 356/85 |
| 4,056,969 | 11/1977 | Barringer | 250/255 |
| 4,136,951 | 1/1979 | Macourt | 356/36 |

Primary Examiner—Vincent P. McGraw

[57] ABSTRACT

A method of detecting the presence of a coating of gaseous molecules on the surface of solid particulate material comprising the steps of entrapping the particulate material in a chemically inert carrier gas, heating the said material to release the gaseous molecules adsorbed on the particles, separating the particles from the carrier gas and the previously adsorbed gas molecules, passing the gases to a plasma, and spectroscopically analyzing the light emitted therefrom to detect the presence of the previously adsorbed gas.

12 Claims, 2 Drawing Figures

U.S. Patent  Sep. 9, 1980  4,221,482

MINERAL PROSPECTING BY THE DETECTION OF RADON OR IODINE

This patent application is a continuation-in-part of patent application Ser. No. 739,110 filed Nov. 5, 1976, now U.S. Pat. No. 4,136,951, entitled: "SEPARATION AND ANALYSIS OF PARTICLE COATINGS".

The present invention relates to a method of separating a chemical coating from particles and provides a method of spectroscopically determining the chemical nature of a coating on particles. The invention has particular relevance to the aerial prospecting for both uranium and related minerals as well as for hydrocarbon deposits which have, as a common feature, the presence of (i) radon (Atomic No. 88 and Atomic Weight 222, a "daughter" product of the radioactive decay of uranium accumulated within the mineral deposit), and (ii) halogen (in particular iodine).

The anomalous occurrence of radon gas around deposits of oil and natural gas, as well as around deposits of uranium and associated minerals, is well known and has been used by numerous prospectors in the search for such deposits. Previous techniques which have been used to detect anomalous radon gas involve drilling shallow holes in the ground from which a sample of air and gas is pumped over a period of time. Radon may be detected by passing the sample through a suitable gamma ray detector which counts the emission of gamma rays by radon as it decays to Bismuth ($Bi_{214}$), and helium.

Because the "half life" of radon is only approximately 3.7 days, there occurs a sharply anomalous concentration of radon over a deposit of the above-mentioned type (the radon rapidly breaks down with time). Accordingly, in the prior art technique mentioned above, the analysis of the gas sample has to be performed continuously as the hole is pumped out. This process is laborious and costly in that it requires considerable on-site equipment and the time taken to cover a reasonable area of ground makes it uneconomic in regional prospecting.

There are several other prior art methods for measuring radon gas concentrations in shallow holes, the most recent of which is known by the trade designation "Trak Etch". This method involves leaving suitable polymeric or photographic materials in such holes, or secured to the bottom of an inverted plastic cup located in such a hole, for several days—during which time $\alpha$, $\beta$ and $\gamma$ rays emanating from the decaying radon, issuing from the ground, produce small apertures in the polymeric material, or cause patterns to be produced in the photographic material (emulsion) according to the rate of release (and hence decay) of the radon gas. The apertures in the polymeric material may be etched with suitable chemicals to increase the size of the apertures to the point where they are visible under a microscope; similarly the photographic material may be developed so as to render the patterns visible. In either case the frequency of the patterns may be ascertained in order to determine the concentration of radon gas released. Measurement-wise, instruments have been developed to count, automatically, the holes in the polymer or photographic film.

The just-mentioned prior art methods require labour intensive, and time consuming, analysis after collection of the exposed material—and are therefore expensive. In consequence such methods are restricted in current use to those areas which are known to be highly prospective and which only require detailed examination over a limited area. Additionally, they (the prior art methods) are also restricted to individual sampling points rather than continuous mobile analysis—which may give rise to errors in that cracks in the earth's surface (such as faults) may be near some holes and not others, and the leakage of radon up these cracks may be detected by the "near" holes (and make interpretation difficult and erroneous). Workers in this field have found that even relatively closely spaced holes do not necessarily give similar readings.

It is among the objects of the invention to provide a novel process whereby the above disadvantages are substantially avoided. The invention is predicated upon my discovery that certain materials, which one would not expect to find in the atmosphere, are in fact present and can be efficiently detected therein—and thereby used to locate deposits of uranium and associated minerals, oil and natural gas. Specifically, I am utilising the quite unexpected presence in the atmosphere of radon (normally not known to rise above the surface of the earth because of its high molecular weight) and halogen, in particular iodine (not expected to be atmospherically located because of its propensity to sublimate and adsorb) for the above purpose.

In its broadest aspect the invention provides a method of detecting the presence of a coating on the surface of particulate material comprising the steps of entrapping coated particulate material in a chemically inert carrier gas, heating the said material to release the coating, passing the released material into a plasma and spectroscopically analysing the light emitted therefrom.

In a further, more specific, aspect, the invention provides a method of detecting the presence of a radon coating on the surface of particulate material comprising the steps of entrapping the particulate material in a chemically inert carrier gas, heating the said material to release the radon adsorbed on the particles, separating the particles from the carrier and radon gases, passing the gases to a plasma and spectroscopically analysing the light emitted therefrom.

In a still further specific aspect the invention provides a method of detecting the presence of a halogen coating, in particular iodine, on the surface of particulate material comprising the steps of entrapping the particulate material in a chemically inert carrier gas, heating the material to release the halogen, in particular iodine, adsorbed on the particles, separating the particles from the carrier and halogen, in particular iodine, gases, passing the gases to a plasma and spectroscopically analysing the light emitted therefrom.

As used above, and hereafter, the term "coating", or "radon coating", or "halogen coating", will be used to cover a wide variety of possible combinations including individual, or numbers, of radon or halogen atoms or molecules (or condensation neuclei) adhering to, or being adsorbed, on the surface(s) of a particle—and, in addition, actual coatings of radon or halogen atoms or molecules (or condensation neuclei) in which the particle itself is partially or substantially completely covered or enveloped with a thin layer of radon or halogen atoms or molecules (or condensation neuclei).

The invention will now be described with sequential reference to (i) preferred sub-generic details, and (ii) a specific operation as illustrated by reference to accompanying drawings. As a general prelude thereto, it is emphasised that such ensuing description is not to be limitatively construed.

RADON DETECTION

Dealing firstly (and sub-generically) with the instant method as applied to the detection of radon, it is initially pointed out that such method enables the continuous detection of radon to be achieved from an aircraft operating at low altitude and speed. This therefore makes the present invention highly suitable for regional prospecting over large areas for anomalous concentrations of radon emanating from surface, sub-surface, or deeply buried deposits of uranium—as well as deposits of oil or natural gas at varying depths. The detection of such anomalous emanations and, with a suitable means of navigation, the accurate determination of their locations within a region, represents a major step in the search for these deposits (and will accurately indicate an area in which further detailed geophysical and geochemical work could be carried out on the ground). In addition, under suitable conditions, the determination of such anomalies may lead to the direct discovery of commercially viable deposits of such minerals or hydrocarbon accumulations.

Proceeding with this form of the present invention, atoms or molecules, or condensation neuclei, of radon gas, which are highly charged, adsorb on the surface of larger particles such as dust at the surface of the earth where the radon gas emanates. The dust particles are elevated into the atmosphere by the action of either wind and/or sun alone or in combination. Such elevated particles could be collected and concentrated by a number of well known methods of subsequent analysis. However unless the analysis is carried out very shortly after the particles are collected, the natural decay of the radon adsorbed on the collected particles will cause the apparent magnitude of the anomaly to be severely reduced once the particle is removed from the area in which the radon gas is being given off. Most importantly, undue delay in analysing the coating may preclude radon being detected at all.

Furthermore, unless the analytical technique used is specific for radon, confusion could result in the interpretation of the results. For example, the Bismuth isotope, having an atomic weight of 214, is a decay product of radon gas which has a half-life of several years. This decay product appears ubiquitously throughout the atmosphere. Therefore if an inadequate technique is used, this can give misleading anomalous radioactivity which may not be due to radon at all.

In the preferred practice of the present invention, only the larger particles, that is those having a dimension greater than 15 to 20 microns, which are located in currents of rising air close to the surface of the ground, are collected by low flying aircraft. These particles are transferred to a chemically inert carrier gas such as helium or argon or a mixture thereof (but which need not be a noble gas) in a manner similar to that used in a conventional mass spectrometer. This manner of transfer involves the projection of the particles, which are heavy relative to the air in which they are carried and collected, into a stream of inert gas which transports them to the desired region i.e. an area in which the radon coating is removed from the surface of the particle. In one form of the invention this transference is effected as illustrated hereafter (in the description with reference to the accompanying drawings). Alternatively, it may be effected by a virtual impaction technique wherein it is the stream of inert gas which, at a predetermined point, is reversed in direction of flow thereby acquiring the particles and transporting them to the said region. The size of the particle acquired by the inert carrier gas stream can be accurately controlled by varying the velocity of the counter-flowing agent and also the distance through which the particles are projected before flow reversal occurs.

The radon coating is released from the particles by neutralizing the electrical charge attaching the atoms or molecules (or condensation nuclei) to the particles and thereby volatilising the coating. This is carried out by heating the particles in a suitable oven i.e. the particles are subjected to pyrolisation, the dust particles in the oven being trapped on a porous sintered filter in which the pore size is finer than the size of the collected particles. In this way the particles are retained by the filter and only the gaseous products of pyrolisation are carried forward in the inert gas stream beyond the filter. The temperature of the oven is as low as possible (a temperature of the order of 150° C.—or less—is invariably adequate) to release the atom(s) or molecule(s) of radon in the coating, by the process of thermophoresis, since at the same time a number of other molecules of varying volatility will also be released. Such molecules may include hydrocarbons and possibly mercury, which volatilised molecules pass on with the stream of gas and radon. These steps are elaborated in the ensuing illustrated description.

Alternatively, the radon coating et al may also be volatilised by the employment of a primary plasma in which the particulate material is retained, and the adsorbed material being volatilised is separated therefrom and passed on to a next stage—where analysis of the volatilised material is carried out.

From the foregoing, it will be observed that a plasma need not be employed to obtain the release or volatilisation of the radon coating (although if it is desired to also analyse the particulate coatings for other adsorbed molecules of low volatility, it may be advantageous to do so). Volatilisation of the adsorbed material may also be accomplished by using a laser if desired.

In the next stage, the released gases and volatilised materials are then transported immediately to a plasma (or secondary plasma) which is viewed by a conventional spectrometer or other suitable instrument which permits the emission or absorption of radon to be observed and measured. The plasma may be either a direct current discharge or an alternating current discharge—and in the latter case, low frequencies, radio frequencies, and microwave frequencies may be used as desired.

When the analysis of the light emitted from the above-mentioned plasma is carried out, in accordance with this embodiment, using the methods of atomic emission spectroscopy, the strongest emission line for radon is at 434.96 nanometers (nm) whilst the next strongest line is at 745.00 nm.

The first of these emission lines is adjacent to the emissions of a well-developed C-H band structure, which emission ends at approximately 433.5 nm at the longer end, and could cause interference. This is particularly relevant if the instant method is used for prospecting for oil or natural gas where hydrocarbons could be adsorbed on the surface of atmospheric particles—and which, in turn, would give significant emission in the well known C-H and C-N bands, the latter of which occurs at approximately 388 nm.

The resolution of the strongest emission line at 434.96 nm will depend on the quality of the particular spectrometer used, but there are several techniques well known to those skilled in the art, for achieving the desired resolution and separation from the above-mentioned C-H band. Additionally the emission line at 745.00 nm or another radon emission line nearby at 705.54 nm, are both relatively free from interference from other continuums and these lines can be used either separately or as a measure of differentiating the radon emission at 434.96 nm from the above-mentioned C-H band emission.

HALOGEN DETECTION

This form of the present invention is described with particular reference to the detection of iodine (especially) and bromine—which (just as in the case of radon) I have found to be both associated with deposits of oil and natural gas et al, and surprisingly present in the atmosphere. Here (referring to iodine) the atoms or molecules (or condensation neuclei) of iodine gas adsorb on the surface of particles such as dust at the surface of the earth where the iodine gas emanates—and (as above) these dust particles are elevated into the atmosphere. Thereafter, entrapment of the particles (in the flow of chemically inert carrier gas), heating (whereby the iodine coating is released), and spectroscopic analysis (whereby errors—that could flow from the natural sublimation of the iodine adsorbed on the entrapped particles—are forestalled) are generally carried out as hereinabove described. In this form of the invention—when the analysis of the light emitted from the plasma is carried out by atomic emission spectroscopy—the most suitable emission line for iodine is at 608.2 nanometers (nm) whilst other suitable lines are at 546.4 nm and 533.8 nm. For bromine, the most suitable emission line is at 478.5 nanometers.

In the detection of iodine by emission spectroscopy, the wave lengths of light produced by electrode decay should not interfere with the iodine spectral lines. It has been found that this is best achieved by the use of electrodes of solid platinum or platinum/indium.

AN ILLUSTRATED EMBODIMENT

Hereunder, the detection of radon gas is described with reference to the annexed illustrative drawings. In again emphasising that such description is by way of example only, it is also recorded that a schematic type of illustration is employed because the individual integers of the illustrated apparatus are themselves conventional in structure.

Figure 2:
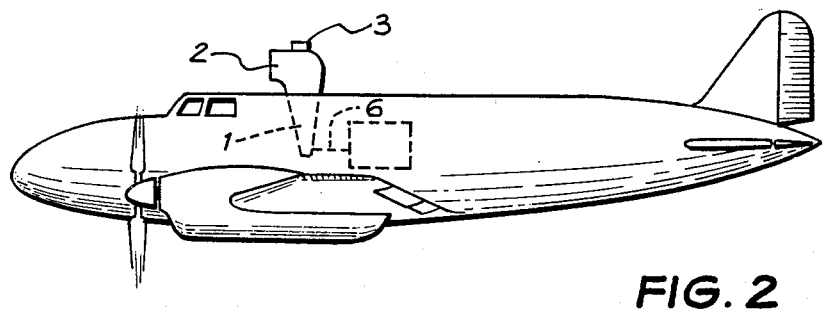

In the drawings:

FIG. 1 schematically depicts an apparatus whereby the instant method may be carried out;

FIG. 2 is a representation of a prospecting aircraft equipped with such an apparatus.

The illustrated apparatus consists of a cyclone concentrator 1 into the mouth 2 of which the air outside the aircraft is forced by reason of its velocity. The particulate matter in the air is concentrated on the conical walls of the cyclone and falls toward a base outlet 4. The remaining air is vented through an outlet 3. A pump 5 draws air off the bottom of cyclone 4 along a tube 6 to a virtual impactor 7, in which a sudden reversal of the direction of flow (of the air) causes the concentrated particles to be projected into and along a pipe 8, which is juxtaposed, and in close proximity to, a similarly-diametered pipe 9 in chamber 10. The reduction of air volume entering impactor 7, compared to that entering the mouth 2 of the cyclone concentrator, may be as much as 1000 times.

Chemically inert carrier gas (specifically helium) is introduced into chamber 10 at constant pressure by means of a valve 11, the suction of the pump 5 causing some of the gas to counter flow along the pipe 8 (thereby preventing the entry of air when the pressure of the valve 11 is suitably corelated to the vacuum of the pump 5). A further pump, 12, draws an aliquot of the inert carrier gas through pipe 9—and thence through the remainder of the apparatus (see below), the flow therethrough being accurately controlled by a valve 16.

Particles projected over the gap between the pipes 8 and 9 and entrapped in the carrier gas in the pipe 9, are carried to a sintered porous filter 13 which is contained in a thermostatically controlled oven 14 (at a temperature of, for example, 100°-200° C.). Size-wise, the particles entering pipe 9 can be adjusted by means of the pressure in chamber 10—which will increase or decrease the counter flow in the pipe 8 (a larger flow will prevent the smaller particles being projected far enough to reach the pipe 9). The size of the smallest particle reaching the sintered filter should be greater than the pass size of the filter. In itself, the filter is removable (from the oven) for cleaning and emptying—and can be sealingly reassembled with equal facility.

The radon gas released from the surface of the particles by thermophoresis, in the oven 14, passes to a two electrode plasma 15 (RF or microwave plasmas would, of course, be equally suitable). This plasma is viewed by a conventional spectrometer or monochromater 17 of which the output is processed and recorded by electronic means 18 coupled to a navigating system 19. In this way, the output of the spectrometer (or monochrometer) can be corelated with the position of the aircraft over the ground.

The apparatus preferably operates at or slightly below atmospheric pressure; for example in the range of 0.5 to 1.0 atmospheres. However, it may operate at much lower pressures (e.g. 0.1 or even 0.01 atmospheres) provided sufficient chemically inert carrier gas is present to transfer the particles into the porous sintered filter.

In the method as just illustrated, the chemically inert carrier gas is specified as helium. However, in lieu thereof, there may be employed any other such gas, noble or otherwise, as exemplified by argon, and mixtures (the latter possibility in turn being exemplified by an argon/helium mixture). The electrodes (of the electrode plasma) are constructed from materials that are free of those elements that are being viewed by the spectrometer; specifically, in the embodiment illustrated, the electrodes are of platinum. In referring to the spectrometer, the opportunity is taken to underscore the fact that the invention is not limited in respect of the type of spectrometer (or method of spectroscopic analysis) employed. Also, whilst discussing alternatives, it will be appreciated that, in lieu of the aircraft (schemetically illustrated in FIG. 2), the apparatus of FIG. 1 could be mounted in a prospecting road vehicle.

In broad summary, the invention, in its primary method aspects, is as hereinbefore broadly defined—with the coated particulate material sequentially subjected to (i) entrapment in a chemically inert carrier gas, (ii) heating and separating treatment to differentiate the coating from the particulate matter—with transfer of the former to a plasma, and (ii) spectroscopic analysis of the plasma. However, the invention should also be understood as embracing:

(a) a method of continuously detecting the presence of a gaseous radon (or iodine) coating upon the surface of particulate material comprising the steps of collecting particulate matter in the atmosphere; concentrating the said material; entrapping the concentrated material in a flow of chemically inert carrier gas; heating the said particulate material to release the radon (or iodine) gas adsorbed thereon; separating the particulate material from the carrier and radon (or iodine) gases; passing the carrier and radon (or iodine) gases to a plasma and spectroscopically analysing the emitted light to varying intensities of emission at wavelengths known to be those of radon (or iodine);

(b) a method comprising the step of collecting particulate material from a selected locality (e.g. by an aircraft flying above said locality); and subjecting the said material to the methods as hereinbefore defined;

(c) a method of separating particulate material from a coating thereon comprising the steps of entrapping coated particulate material in a chemically inert carrier gas, subjecting the entrapped material to pyrolisation whereby the coating is released from the particulate material by thermophoresis, and separating the particulate material and released coating;

(d) an apparatus for separating particulate material from a coating thereon comprising in combination, means for collecting the particulate material, means whereby the collected particulate material is entrapped in a chemically inert carrier gas, means for effecting pyrolisation, and release, of the entrapped coated particulate material, and means for separating the released coating from the particulate material;

(e) an apparatus for detecting the presence of a coating on the surface of particulate material comprising in combination, means for collecting the particulate material, means whereby the collected particulate material is entrapped in a chemically inert carrier gas, means for effecting pyrolisation, and release, of the entrapped coated particulate material, means for separating the released coating from the particulate material, and a plasma to which the separated coating is conveyed and within which it is spectroscopically examined.

The claims defining the invention are as follows:

1. A method for prospecting for valuable mineral deposits comprising the steps of
   collecting atmospheric particulate matter,
   concentrating the particulate matter,
   entrapping the concentrated particulate matter in a flow of chemically inert carrier gas,
   releasing any radon or iodine gas adsorbed on said particulate matter by neutralizing the electrical charge attaching the gas atoms to the particles,
   separating the particulate matter from the carrier gas and from any released gas,
   passing the carrier and released gases to a plasma,
   and spectroscopically analyzing the emitted light for emissions at one or more wavelengths known to be characteristic of radon or iodine.

2. A method for prospecting for valuable mineral deposits comprising the steps of
   collecting atmospheric particulate matter,
   concentrating the particulate matter,
   entrapping the concentrated particulate matter in a flow of chemically inert carrier gas,
   releasing any radon gas adsorbed on the particulate matter by neutralizing the electrical charge attaching the radon atoms to the particulate matter,
   separating the particulate matter from the carrier gas and any released radon gas,
   passing the carrier and radon gases to a plasma,
   and spectroscopically analyzing the emitted light for emissions at one or more wavelengths known to be those of radon.

3. A method for prospecting for valuable mineral deposits comprising the steps of
   collecting atmospheric particulate matter,
   concentrating the particulate matter,
   entrapping the concentrated particulate matter in a flow of chemically inert carrier gas,
   releasing any iodine gas adsorbed on the particulate matter by neutralizing the electrical charge attaching the iodine atoms to the particulate matter,
   separating the particulate matter from the carrier gas and any released iodine gas,
   passing the carrier and iodine gases to a plasma,
   and spectroscopically analyzing the emitted light for emissions at one or more wavelengths known to be those of iodine.

4. A method as claimed in claim 1 wherein
   the neutralization of the electrical charge attaching the gas atoms to the particulate matter is carried out by heating the particulate matter to a temperature in a range up to 200° C.

5. A method as claimed in claim 1 wherein
   the concentrated particulate matter is sorted to entrap only those particles of the concentrated particulate matter above 15 microns in diameter in the flow of chemically inert carrier gas for subsequent analysis.

6. A method as claimed in claim 5 wherein
   the selection of particles above 15 microns in diameter is accomplished by a flow reversal of the chemically inert carrier gas accomplished as the concentrated particles are entrapped in the flow of carrier gas.

7. A method as claimed in claim 5 wherein
   the separation of the particulate matter from the carrier gas and the released gas is accomplished by mechanical filtration.

8. A method as claimed in claim 1 wherein
   the atmospheric particulate matter is collected by an aircraft and wherein
   the subsequent steps of the method are carried out on the aircraft on a continuous basis as the aircraft flies over the terrain where the particles are collected.

9. A method as claimed in claim 8 wherein
   the results of the continuous operation of the method in conjunction with aircraft travel is recorded, and wherein
   the aircraft position is continuously recorded so as to provide a correlated record between aircraft position and the analysis of the materials derived from the collected particulate matter.

10. Apparatus for prospecting for valuable mineral deposits comprising means for collecting atmospheric particulate matter,
    means for concentrating the particulate matter,
    means for entrapping the concentrated particulate matter in a flow of chemically inert carrier gas,
    an oven for heating the particulate matter up to a temperature in a range below 200° C. for releasing any radon or iodine gas adsorbed on the particulate matter by neutralizing the electrical charge attaching the gas atoms to the particulate matter, means for separating the particulate matter from the carrier gas and any released radon or iodine gas, said separating means comprising a mechanical filter positioned within said oven, a two-electrode plasma apparatus for receiving the carrier and the released radon or iodine gases for spectroscopic analysis, and a spectrometer positioned and arranged to analyze the light emitted from the plasma apparatus for emissions at one or more wavelengths known to be those of radon or iodine.

11. An apparatus as claimed in claim 10 wherein the electrodes of said plasma apparatus are comprised of platinum.

12. Apparatus as claimed in claim 10 which is especially adapted for installation in an aircraft and which is operable for continuous analysis of atmospheric particulate matter gathered during flight of the aircraft, said apparatus including continuously operable recording means connected to said spectrometer for continuously recording the results of the analysis, said recording means also being arranged to be connected to the navigation system of the aircraft for deriving aircraft position information from the navigation system and for continuously recording said position information in conjunction with said analysis information to provide a correlated record.

* * * * *